(12) United States Patent
Zhou et al.

(10) Patent No.: US 7,458,936 B2
(45) Date of Patent: *Dec. 2, 2008

(54) SYSTEM AND METHOD FOR PERFORMING PROBABILISTIC CLASSIFICATION AND DECISION SUPPORT USING MULTIDIMENSIONAL MEDICAL IMAGE DATABASES

(75) Inventors: Xiang Sean Zhou, Plainsboro, NJ (US); Dorin Comaniciu, Princeton Junction, NJ (US); Alok Gupta, Bryn Mawr, PA (US); Visvanathan Ramesh, Plainsboro, NJ (US); Bhavani Duggirala, Bellevue, WA (US); Diane Paine, Redmond, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 700 days.

This patent is subject to a terminal disclaimer.

(21) Appl. No.: 10/703,024

(22) Filed: Nov. 6, 2003

(65) Prior Publication Data

US 2004/0193036 A1 Sep. 30, 2004

Related U.S. Application Data

(60) Provisional application No. 60/454,113, filed on Mar. 12, 2003, provisional application No. 60/454,112, filed on Mar. 12, 2003.

(51) Int. Cl.
*A61B 8/00* (2006.01)
(52) U.S. Cl. ............... 600/437; 600/407; 600/450; 128/920; 128/924; 706/46

(58) Field of Classification Search ......... 600/300–301, 600/407, 409, 425, 427, 437, 443, 447, 473, 600/476, 481, 483, 485, 500, 504, 509, 513, 600/529, 544, 549; 128/920, 924; 706/46
See application file for complete search history.

(56) References Cited

U.S. PATENT DOCUMENTS

| | | | |
|---|---|---|---|
| 5,235,510 A | 8/1993 | Yamada et al. | 364/413.02 |
| 5,799,100 A | 8/1998 | Clarke et al. | 382/132 |
| 5,799,101 A * | 8/1998 | Lee et al. | 382/133 |
| 6,032,678 A | 3/2000 | Rottem | 128/920 |

(Continued)

OTHER PUBLICATIONS

"Efficient Interpretation Policies", Isukapalli et al., in Proc. IJCAI, 2001.

(Continued)

*Primary Examiner*—Ruth S Smith
*Assistant Examiner*—Jonathan G Cwern

(57) ABSTRACT

A system and method for providing decision support to a physician during a medical examination is disclosed. Data is received from a sensor representing a particular medical measurement. The received data includes image data. The received data and context data is analyzed with respect to one or more sets of training models. Probability values for the particular medical measurement and other measurements to be taken are derived based on the analysis and based on identified classes. The received image data is compared with training images. Distance values are determined between the received image data and the training images, and the training images are associated with the identified classes. Absolute value feature sensitivity scores are derived for the particular medical measurement and other measurements to be taken based on the analysis. The probability values, distance values and absolute value feature sensitivity scores are outputted to the user.

19 Claims, 7 Drawing Sheets

U.S. PATENT DOCUMENTS

| | | | |
|---|---|---|---|
| 6,301,579 B1* | 10/2001 | Becker | 707/102 |
| 6,314,322 B1* | 11/2001 | Rosenberg | 607/17 |
| 6,320,976 B1 | 11/2001 | Murthy et al. | 382/128 |
| 7,087,018 B2* | 8/2006 | Comaniciu et al. | 600/300 |

OTHER PUBLICATIONS

"Filters, Wrappers and a Boosting-Based Hybrid for Feature Selection", S. Das, in Proc. ICML, 2001.

"Vision for Mobile Robot Navigation: A Survey", DeSouza et al., IEEE Transactions on Pattern Analysis and Machine Intelligence, vol. 24, No. 2, Feb. 2002, pp. 237-267.

"Some Slutions to the Missing Feature Problem in Vision", Ahmad et al., Advances in Neural Information Processing Systems 5, Morgan Kaufmann Publishers, San Mateo, CA.

"Autonomous Exploration Using Multiple Sources of Information", Moorehead et al., Proceedings of the 2001 IEEE Int'l Conference on Robotics & Automation, Seoul, Korea, May 21-26, 2001, pp. 3098-3103.

"A Mathematical Programming Approach to the Kernel Fisher Algorithm", Mika et al., in NIPS 13, 2001.

"Using Mutual Information for Selecting Features in Supervised Neural Net Learning", R. Battiti, IEEE Transactions on Neural Networks, vol. 5, No. 4, Jul. 1994, pp. 537-550.

"Learning from Incomplete Data", Ghahramani et al., in NIPS6, 1994.

"Active Sensing for Robotics—A Survey", Mihaylova et al, in Proc. 5th Int'l Conf. on Numerical Methods and Applications, 2002.

"Learning Active Vision", Kappen et al., in Proc. ICANN, Oct. 1995.

"Active Vision for Complete Scene Reconstruction and Exploration", Marchand et al., IEEE Transactions on Pattern Analysis and Machine Intelligence, vol. 21, No. 1, Jan. 1999, pp. 65-72.

"Transinformation for Active Object Recognition", Schiele et al., ICCV, 1998.

"Information Theoretic Sensor Data Selection for Active Object Recognition and State Estimation", Denzler et al., IEEE Trans. On Pattern Analysis and Machine Intelligence, vol. 24, No. 2, Feb. 2002, pp. 145-267.

"Feature Space Trajectory Methods for Active Computer Vision", Sipe et al., IEEE Trans. On Pattern Analysis and Machine Intelligence, vol. 24, No. 12, Dec. 2002, pp. 1634-1643.

"Viewpoint Selection by Navigation through Entropy Maps", Arbel et al., ICCV, Corfu, Greece, Sep. 1999.

"Training Neural Networks with Deficient Data", Tresp et al., Advances in Neural Information Processing Systems 6, San Mateo, CA, Morgan Kaurman, 1994.

"Medical Image Databases: A Content-based Retrieval Approach", American Medical Informatics Association, http://www.pubmedcentral.nih.gov/articlerender.fcgi?artid=61234.

"Classification Driven Semantic Based Medical Image Indexing and Retrieval", Liu et al., 1998 Carnegie Mellon University.

"Fast and Effective Retrieval of Medical Tumor Shapes", Korn et al., IEEE Transactions on Knowledge and Data Engineering, vol. 10, No. 6, Nov./Dec. 1998, pp. 889-904.

"Joint Induction of Shape Features and Tree Classifiers", Geman et al., May 1996.

"Image-guided decision support system for pathology", Comaniciu et al., Machine Vision and Applications (1999), pp. 213-224.

"Content-Based Retrieval from Medical Imaging Databases: A Synergy of Human Interaction, Machine Learning and Computer Vision", Brodley et al., 1999, American Assoc. for Artificial Intelligence.

"Toward Validation Databases for Medical Imaging: Engineering a Scientific Rendezvous", Yoo, National Library of Medicine, National Institutes of Health, Bethesda, MD.

"Content-Based Image Retrieval in Medical Applications: A Novel Multi-Step Approach", Lehmann et al., Part of the IS&T/SPIE Conf. on Storage and Retrieval for Media Databases 2000, San Jose, CA, Jan. 2000, SPIE vol. 3972, pp. 312-320.

U.S. Appl. No. 10/654,509, filed Sep. 3, 2003 entitled "Remote Assistance for Medical Diagnostic Ultrasound".

* cited by examiner

SYSTEM AND METHOD FOR PERFORMING PROBABILISTIC CLASSIFICATION AND DECISION SUPPORT USING MULTIDIMENSIONAL MEDICAL IMAGE DATABASES

CROSS REFERENCE TO RELATED APPLICATION

This application claims the benefit of U.S. Provisional Application Ser. No. 60/454,113, filed on Mar. 12, 2003, and U.S. Provisional Application Ser. No. 60/454,112, filed on Mar. 12, 2003, which are incorporated by reference in their entirety.

FIELD OF THE INVENTION

The present invention is directed to a system and method for providing decision support using multidimensional medical image databases, and more particularly, to a Computer Aided Diagnosis (CAD) system for that is capable of learning from previously labeled patient data to assist in decisions regarding further tests and/or diagnosis of a patient.

BACKGROUND OF THE INVENTION

Much attention and research has been paid toward medical applications using content-based image retrieval techniques. Some work has been done toward summarization of echocardiogram videos using visual contents such as color, shape, and the tracing of the Electrocardiogram (ECG) signal. However, limited efforts have been spent on diagnosis support of cardiomyopathies using echocardiography, advanced statistical classification and learning techniques.

Conventional computer-aided diagnosis (CAD) systems treat different inputs independently, such as between components of a numerical feature vector, between vectors of different modalities, and between numerical and symbolic inputs. Furthermore CAD systems make decisions in a sequential, rule-based, tree-like fashion. The disadvantage to this approach is that when the numerical feature inputs are unreliable, which is usually the case when using automated feature extraction instead of manual extraction; the system performance can degrade dramatically, depending upon the order in which the sequential decisions are arranged.

Another drawback of the traditional decision tree approaches is that each decision can only be made along existing feature dimensions, which is in turn limited by the prior selection of the feature components, without linear or nonlinear transformation invariance. Some recent general approaches using classification trees extends the traditional paradigm for decision tree construction and can use an aggregation of multiple trees to achieve higher capabilities.

There is a need for a CAD system capable of implementing probabilistic classification, content-based similarity comparisons and machine learning algorithms using multidimensional medical image databases in order to assist a medical professional to reach a medical diagnosis.

SUMMARY OF THE INVENTION

The present invention is directed to a system and method for providing decision support to a physician during a medical examination is disclosed. Data is received from a sensor representing a particular medical measurement. The received data includes image data. The received data and context data is analyzed with respect to one or more sets of training models. Probability values for the particular medical measurement and other measurements to be taken are derived based on the analysis and based on identified classes. The received image data is compared with training images. Distance values are determined between the received image data and the training images, and the training images are associated with the identified classes. Absolute value feature sensitivity scores are derived for the particular medical measurement and other measurements to be taken based on the analysis. The probability values, distance values and absolute value feature sensitivity scores are outputted to the user.

BRIEF DESCRIPTION OF THE DRAWINGS

Preferred embodiments of the present invention will be described below in more detail, wherein like reference numerals indicate like elements, with reference to the accompanying drawings.

DETAILED DESCRIPTION

The present invention is a CAD system that implements a number of techniques to assist in decisions regarding further tests or diagnosis for new patients. The system utilizes training models comprising contextual data, such as patient data, image data and other information that is analyzed by the system prior to a patient's examination (i.e., testing phase). During the training phase, the system takes as inputs features extracted from images, in the form of numerical values or vectors, as well as symbolic labels (e.g., keywords extracted from patient records), and also takes as class labels (or ground truth) the doctor's diagnosis for each patient, and uses probabilistic classification and machine learning algorithms to formulate linear and nonlinear decision boundaries or models for different diseases or conditions. The inputs extracted from the images may include data regarding color and texture that has been converted to numerical values.

During the testing phase, the system takes as inputs features vectors and symbolic labels, and makes a decision or suggestion in the form of one or more class labels with associated beliefs or probabilities. The training and the testing phase are not necessarily separated and fixed. The system is interactive, and the two phases can be interwoven in that a doctor can adjust or retrain the system during the testing phase, by correcting the labels or changing the probabilities or system parameters.

Figure 1:
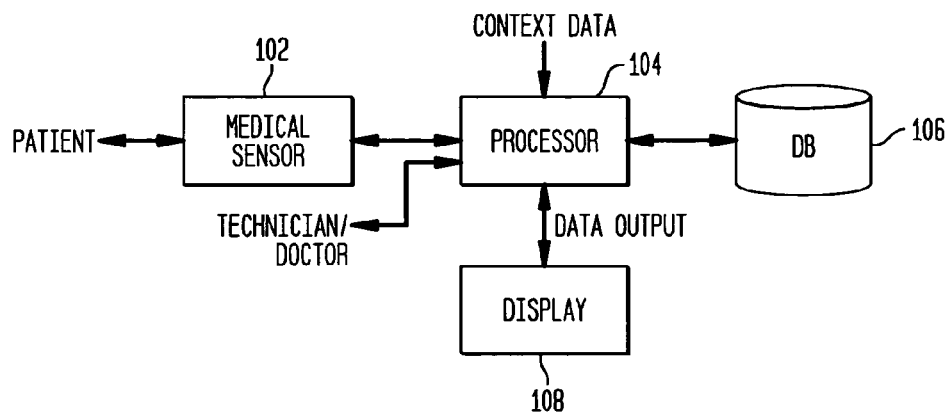
FIG. 1 is a block diagram of a system for implementing a method for conditional feature sensitivity analysis in accordance with the present invention.

FIG. 1 illustrates an exemplary architecture of an echocardiograph system that uses techniques for assisting a physician in providing a medical diagnosis in accordance with the present invention. A medical sensor 102, such as an ultrasound transducer is used to perform an examination on a patient. The sensor 102 is used to obtain medical measurements consistent with a particular medical examination. For example, a patient experiencing heart problems may have an echocardiogram performed to help diagnose the particular heart ailment. In such an instance, the medical sensor 102 may be an ultrasound transducer. An ultrasound system provides two- or three-dimensional images of the heart from various perspectives.

The present invention will be described in detail in the context of performing an echocardiogram examination. However, it is to be understood by those skilled in the art that the present invention can be used in conjunction with other medical examinations such as, but not limited to, breast cancer detection examinations, prenatal ultrasound examinations or another type of medical examination in which a diagnosis is being determined.

The information obtained by the sensor 102 is communicated to a processor 104 which may be a workstation or personal computer. The processor 104 converts the sensor data into an image that is communicated to display 108. The display 108 may also communicate other graphical information or tables of information relating to the image. In accordance with the present invention, the processor 104 is also provided with context data which is used in conjunction with the sensor data to determine what, if any, further measurements need to be taken by the sensor 102 in order to provide a proper medical diagnosis.

Upon receipt of the data from the medical sensor 102, the processor 104 retrieves training models from a database 106 in order to perform various analyses as will be described in greater detail hereinafter. These analyses can include probabilistic classification, similarity comparison and feature sensitivity techniques. In addition to data from the medical sensor, the processor 104 may also receive other data inputs. For example, the processor may receive data from the technician, sonographer or physician performing the medical procedure. The processor 104 may also receive other measurements or system data to be considered during the analyses. The training models contain a collection of data measurements relating to one or more particular medical conditions. For example, the database may contain a plurality of distribution data points relating to the likelihood of a patient having Dilated Cardiomyopathy (DCM) or a normal heart condition (nonDCM). Such data may include measurements pertaining to the size of the heart, the thickness of the heart walls and the level of blood flow to and from the heart.

Figure 2:
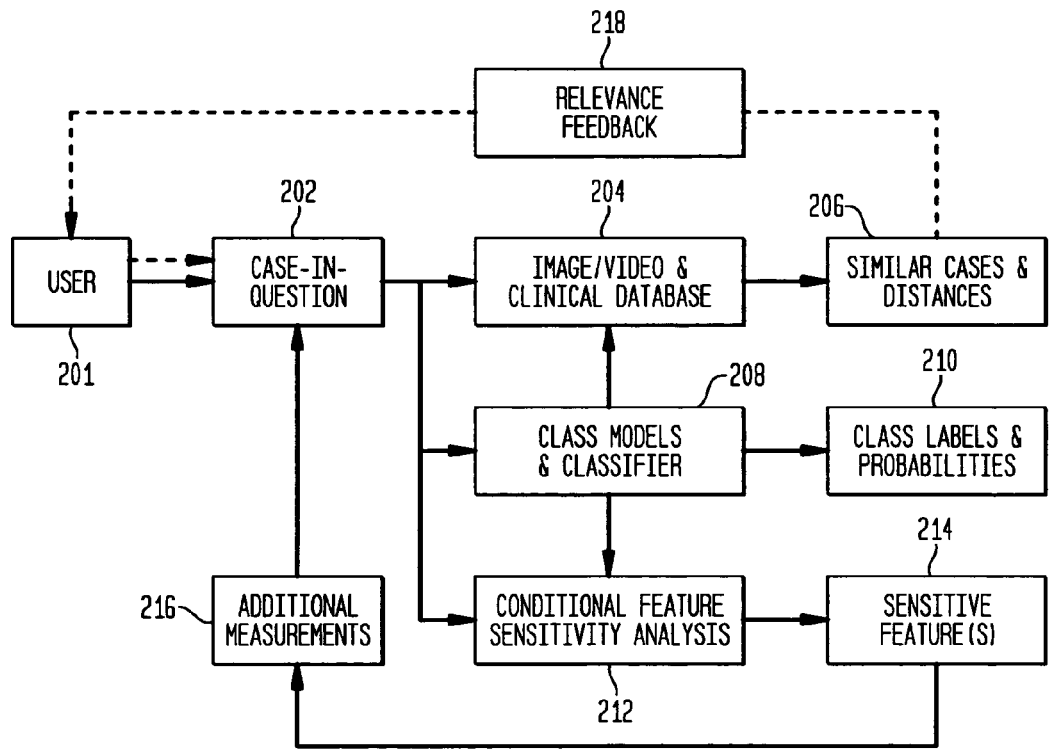
FIG. 2 is a functional block diagram illustrating the overall process for diagnosis support.

Referring to FIG. 2, a block diagram is shown that illustrates the major components of the system of the present invention. The system comprises three major components; probabilistic classification (208, 210), similar case comparison (204, 206, 218), and feature sensitivity analysis (212, 214, 216) for data acquisition guidance. Each component takes all the relevant information from the case in question 202 (both missing and uncertain features) and any user input 201. The measurements used by these components are obtained from measurements taken by sonographers and physicians in a clinical report (e.g., ejection fraction, LV dimension, LA dimensions, aorta, septum and posterior wall thickness, and some hemodynamic measurements such as pulmonary acceleration time and systolic RV pressure, etc.). In addition, automatic tracking algorithms can be used to extract such information plus motion and dynamics features for regional wall segment analysis toward the diagnosis of ischemia and infarction, etc.

Each component analyzes the information and returns an output. In the case of probabilistic classification, an indication of the probability of the presence of a certain disease or condition is provided. In the case of similar case comparison, a list of training images is provided with an indication of the likelihood of a match with the case in question 206. In the case of feature sensitivity analysis, a list of sensitive features 214 that provides a list of additional measurements 216 that should be measured next, to maximally reduce uncertainty in classification is provided.

As indicated above, the first component of the system is probabilistic classification. The purpose of probabilistic classification is to give a "second opinion" suggestion to the cardiologist or sonographer based on the current knowledge about the case in question. A probabilistic output is preferred over a deterministic one due to the complicated nature involved in reaching a medical decision.

In accordance with the present invention, induction algorithms are chosen that can learn probabilistic models from the training data. For linearly separable classes, non-parametric discriminant analysis is used; for nonlinear class boundaries, kernel discriminant analysis is used. In both cases, generative modeling in the reduced discriminative space is used to obtain likelihood maps for every class.

Non-parametric discriminant analysis uses as the between class scatter matrix the sum of the scatter matrices between every point and its top k nearest neighbors from other classes, where $k \leq n$, and n is the total number of points from the other classes. In the present invention, $k=n/2$ is used. The reason for choosing non-parametric analysis instead of the regular discriminant analysis is because, on one hand, it can reduce the influence from outliers; and on the other hand, it can provide more effective dimensions for later class likelihood modeling.

The kernel discriminant has been shown to have comparable performance as a Support Vector Machine (SVM). In addition, it can provide a low dimensional, non-linearly transformed subspace, in which simple probability models can be built to reliably represent the class distributions. Kernel selection is an ongoing research topic and we use RBF kernel with an empirically chosen spread.

Figure 3:
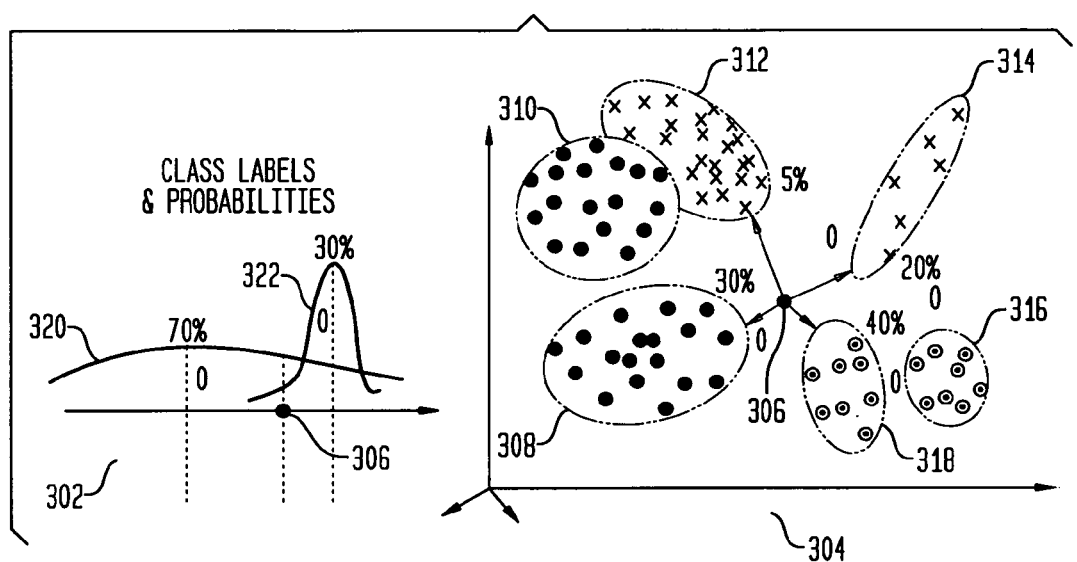
FIG. 3 is graphs illustrating a Bayesian-like decision process that is adopted by the present invention.

FIG. 3 illustrates a Bayesian-like decision process adopted by the present invention. Two graphs 302, 304 are illustrated which show a measurement 306 from the case in question and a group of potential classes in which the measurement may be classified. The first graph 302 is a Gaussian representation of groupings 308-318 of the second graph 304. Measurement 306 is the measurement corresponding to the case in question 202. The second graph 304 is a Bayesian representation of the potential groupings or classes to which measurement 306 may be included. By using basic distance calculations the closest points within the classes are identified. Based on the distances, probabilities are calculated to indicate the likelihood that measurement 306 belongs to a particular class. However when distance calculations are performed on the Gaussian representation, the probability calculations have different results and the measurement 306 may be associated with a different class.

Figure 4:
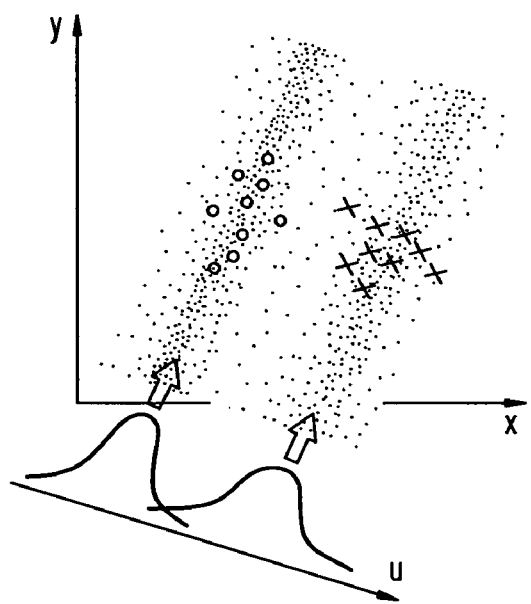
FIG. 4 is a graph illustrating a likelihood back projection in accordance with the present invention.

Referring to FIG. 4, a likelihood map is back-projected into the original space. This implies that approximate $P(x, y|C)$ can be approximated by $P(u|C)$, where $u=f(x, y)$ is the discriminant(s). f can be nonlinear. A "likelihood spilling" effect is shown, i.e., infeasible regions in the original feature space may receive high likelihood. To minimize this effect, sampling in the original space is confined in the feasible range of the features.

In collecting data to be used for training data, it is often necessary to expect missing feature values in the training data. One solution is to apply data imputation (through sampling) to fill in missing (or uncertain) values for feature(s) y, based on p(y|x) where x represents the remaining features with known values. p(y|x) can be estimated on the training data.

Due to estimation error in p(y|x), data imputation will introduce additional noise especially outliers. Robust estimation is desirable for both data normalization and class modeling to minimize the influence from such outliers. A robust estimate for location is the median and for the scale we use 0.7413*IQR, where IQR is the interquartile range (assuming data normality). Regularization is necessary for discriminant analysis with relatively small number of training samples and any conventional regularization method may be used.

The present invention determines probabilistic classifications and makes probabilistic decision in high-dimensional space, instead of doing the decision along each measurement dimension individually in a sequential. With sufficient training samples, probabilistic learning algorithms can also support differential diagnosis. For example, large margin classifiers or discriminant analysis can provide the subset (or subspace) of features that can be used to discriminate two or more confusing diseases. The learned discriminative feature subset also indicates to the doctor (or the trainee, when the system is used as a teaching or training tool) "the most informative test" that shall be done next to clear the diagnostic confusion with the highest probability.

Figure 9:
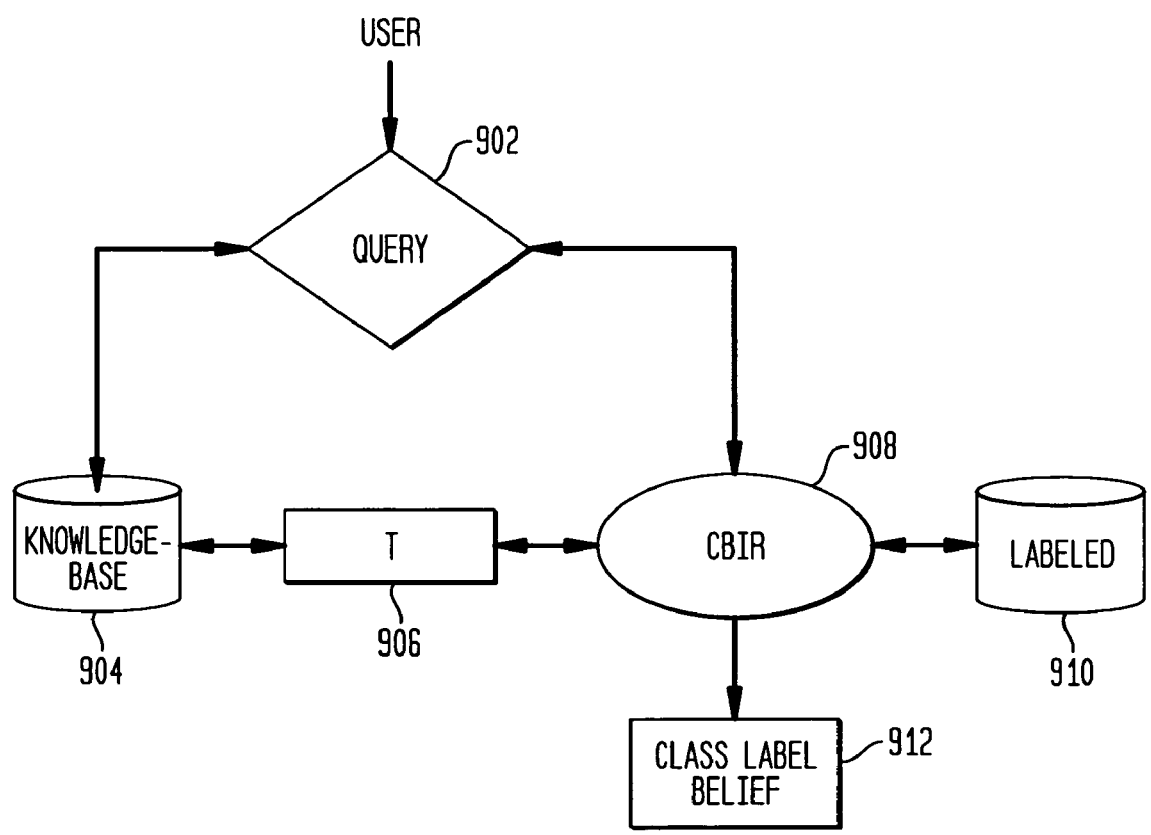
FIG. 9 is a system block diagram that illustrates a high level model of a method for providing probabilistic classification that incorporates a knowledgebase and learning algorithms in accordance with the present invention.

FIG. 9 illustrates a system diagram that depicts a method for providing probabilistic classification that incorporates a knowledgebase and learning algorithms in accordance with the present invention. The system makes joint use of patient data (textual, symbolic) and feature vectors (numerical, continuous) contained in a labeled database 910. A knowledgebase 904 is used to store high-level decision rules learned from the doctors. Examples of such decisions rules can include rules pertaining to cardiac wall segment motion that can help in the diagnosis of coronary artery disease. In addition, rules pertaining to the normal healthy range and distribution of a certain feature, such as ejection fraction of the human heart may be included.

Specifically designed transformations maintained in block T 906 are applied to quantify such knowledge in the feature space in terms of numerical representations or similarity (or distance) metrics, etc. Such transformations may include the extraction of wall motion information from images, and the transformation of such motion into values that can be related to the localization and severity of coronary artery disease. Other transformations may include the transformation of the range and distribution into a uniform or Gaussian distribution as the prior distribution for that feature.

Anatomy and diagnostic rules that are applied by a physician are part of the database in a schema. A pattern analysis engine (not shown) may extract from this schema appropriate keywords, and/or part/whole relations between those keywords, related to a Content Based Image Retrieval (CBIR) function. These keywords and attributes of interest to CBIR 908 may include specific information about organ geometry, geometric arrangements, etc. The system utilizes such information to devise feature spaces of relevance to CBIR 908. The system also attempts to automate the choice of feature space as much as possible through automatic compilation of the knowledge into an intermediate data structure that encodes spatial relationships, spatio-temporal intensity characteristics in objects of interest.

The CBIR engine provides decision support based on a combination of rules-based expert knowledge (properly transformed), example-based learning, discriminative features (i.e., tests) for confusing classes, and other classification boundaries in the joint annotation and feature/measurement space.

In accordance with the present invention, similar disease cases can be considered side-by-side in order to render a medical diagnosis, which can be especially helpful for those medical practitioners who are less experienced. Preferably, the training data comprises a large collection of disease cases with leading experts' diagnosis, annotations, and explanations. Comparison with such data can be used for pure training or research purposes as well as medical diagnosis.

The present invention uses content-based similarity comparison techniques to compare images from the case in question to images included in the training data to providing guidance in deriving a medical diagnosis. Similarity measurements can be defined either in the original feature space (Cartesian space) or in the classification space (reduced discriminative space).

Figure 5:
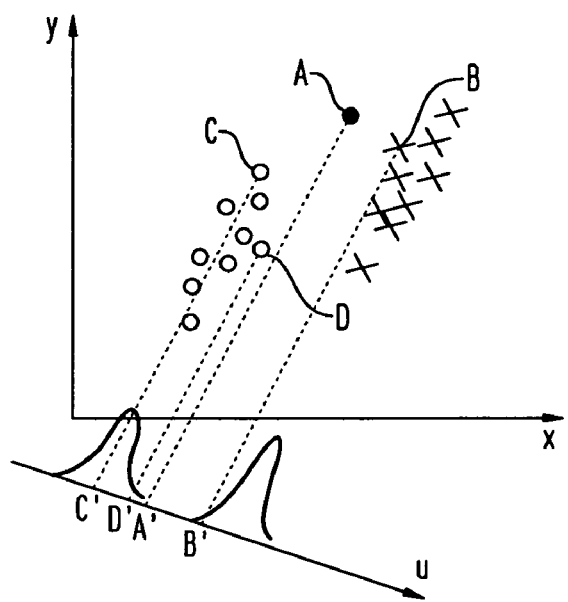
FIG. 5 is a graph illustrating similarity measurements in Cartesian space and reduced discriminative space in accordance with the present invention.

FIG. 5 depicts the difference between these two measurements. Given the case in question denoted by the point A, point B is the nearest neighbor in the original space (X-Y space); point C is the nearest neighbor from the "Circle" class. However, in a linear discriminative subspace (U-space), point D is the nearest neighbor to A. This is in accordance to the Bayesian classification principle adopted in this system.

Figure 6:
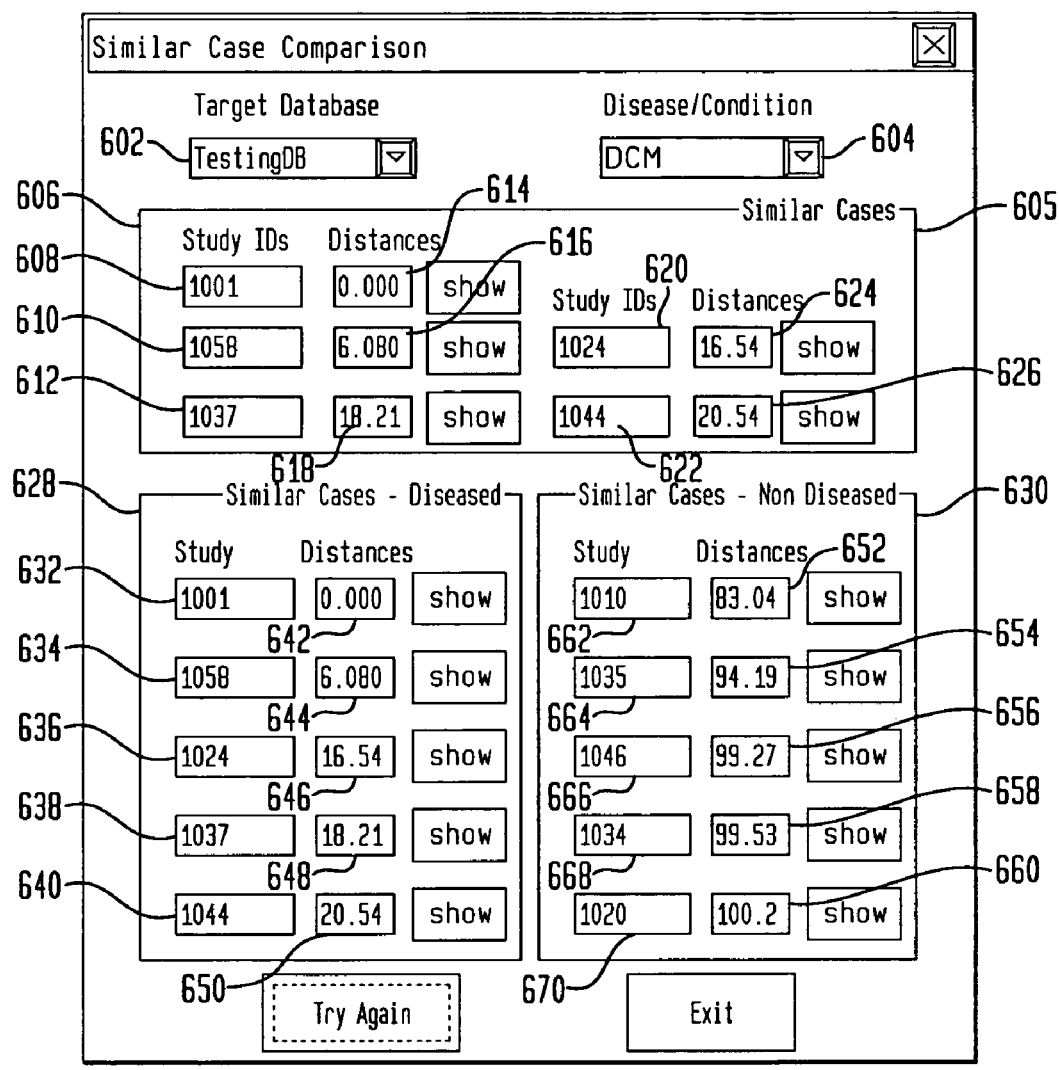
FIG. 6 is an exemplary user interface for the system of the present invention that illustrates the similar case comparison results in accordance with the present invention.

FIG. 6 illustrates an exemplary user interface for indicating similar cases for case 1001, without or with considering and grouping by class labels, respectively. A user can use input 602 to select a database from which training data (i.e., images) are to be considered. The user can also use input 604 to specify the particular disease or condition to be considered.

As indicated above, the case in question corresponds to image 1001. For each class considered, distance measurements are calculated. The five images having the shortest distance measurements are displayed for each class. For the first class or generally similar cases 605, the images are identified in spaces 606, 608, 610, 620 and 622 and their corresponding distances are represented in spaces 616, 618, 620, 624 and 626 respectively. The distances are measured in the discriminative classification space.

Also shown on the interface are the similar cases for the diseased class 628 and the non-diseased class 630. The diseased class 628 indicates the images in spaces 632-640 and the distance measurements in spaces 642-650. The non-diseased class 630 indicates the images in spaces 652-660 and the distance measurements in spaces 662-670. The distance measurements indicate that cases from the DCM class all have much small distances (<21) as compared to the distances to the cases in the nonDCM class (>83), which can be used as a strong indication of DCM for 1001. On the other hand, for borderline cases, similar distances in the two classes can be observed. Any images of interest to the physician can be displayed by selecting the "show" input associated with the particular image.

The content-based similarity comparison techniques can also incorporate relevance feedback provided by the user (218 of FIG. 2). The relevance feedback algorithm can take a relatively small number of training examples and learn an informative and discriminative subset or subspace in the original feature space, with either linear or nonlinear transforms. The physician can compare the case-in question with patient cases selected by the system based on the nearest neighbor measurement. Each patient case comprises one or more images of a particular patient as well as context data and feature categories. The physician can then select a subset of the patient cases that the physician determines to be most relevant to the case in questions. Such selection is typically based on more abstract criteria than that used by the content-based similarity comparison algorithm. A selected patient case may not be based on quantifiable information (i.e., the selection may be based on the physician's experience and prioritization based on familiarity with the particular disease and the case-in-question). For example, the physician may identify a portion of the image that he or she feels is relevant. In addition, the physician can study the movement of the heart as well as shape of arteries and use that information to select particular patient cases.

The system then uses the physician's patient case selections to redefine the area in which the nearest neighbor is to be calculated. In other words, the parameters for determining the nearest neighbor are redefined based on the physician's selection in order to retrieve a set of patient cases that are more relevant to the case-in-question than the original retrieved set of patient cases. Using conventional content based image retrieval techniques (e.g., using different weighting schemes on color/intensity, texture, shape, or motion attributes in the selected portion, combined with other contextual attributes), the system can re-search the database and retrieve a new set of patient cases based on the new criteria. The relevance feedback process can be an iterative process, in that the physician can look at the new set of images and further refine the search again based on the content of one or more of the images.

The present invention also uses conditional feature sensitivity analysis for real-time guidance during the medical data acquisition process. Feature sensitivity analysis allows the system to proactively recommend next feature(s) to measure based on current knowledge, in a real-time interactive setting during, for example, an echocardiogram examination.

Feature sensitivity analysis assigns feature sensitivity values to a set of potential measurements to be taken during a medical procedure in order to select those measurements having the highest feature sensitivity thereby achieving a proper medical diagnosis with a minimal number of measurements being taken. Feature selection is essentially a search for the most sensitive feature subset for the purpose of improved classification accuracy and a significantly reduced feature set. The present invention addresses feature selection that further includes a specific test input or case-in-question along with a context. For any given medical diagnosis, all features for a given case are presumed to be uncertain but to different degrees—a measured feature (e.g., the visible patterns from the current camera angle) contains lower uncertainty, while a missing feature (e.g., the unseen or self-occluded parts of an object) has maximal uncertainty. Then, the question is: "given an induction algorithm, a labeling on a training set, and some contextual information for the case-in-question, what is the relative sensitivity for all features?" In other words, if more measurements are taken, either on unmeasured features, or to increase the accuracy of measured features, what additional measurements should be taken? The present invention is directed to how to evaluate the importance or sensitivity of the features or measurements, as well as how to deal with uncertainty in the contextual features, which will be described in more detail hereinafter.

Even for a case with all features measured, feature sensitivity analysis can still be applied based on the observation that no measurement is precise. By assuming a distribution around every measurement values (based on prior knowledge on noise or measurement equipment parameters), feature sensitivity scoring can be performed. A measured feature with a relatively high sensitivity score should be re-measured first to achieve higher certainty in classification.

The present invention assumes a uniform distribution (with maximal entropy) around the measured value to model the uncertainty in measurement. The width of the distribution is set to be proportional to the standard deviation of that feature over a large training data set (e.g., 0.2σ, this is a parameter that is tunable by the user for different cases and features).

The absolute value of the sensitivity score is significant: in some cases there may be no sensitive feature at all while in others all features are sensitive. The value range of the sensitivities needs to be determined to properly display the result to the user.

The information gain for all features has a constant upper bound, $IG_i \leq \log(K)$, where i is the feature index, K is the number of classes, log(K) is equal to the maximum value and $IG_i$ represents the input value.

This bound is reached when the $i^{th}$ feature is "fully active" in that before its measurement, all classes are equally probable ($P_k = 1/K$), and the entropy is:

$$\sum_{k=1}^{K} P_k \log\left(\frac{1}{P_k}\right) = K \frac{1}{K} \log(K) = \log(K) \quad (1)$$

and after its measurement, the class label can be assigned with no uncertainty (i.e., zero entropy). Therefore, $$IG_i = \log(K) - 0 = \log(K). \quad (2)$$

The above bound can be reached only under rather extreme cases. In most cases, the sensitivity in terms of IG is usually much smaller than this bound. A logarithmic transformation is performed to get a score, S, which is more practically visible under a linear scale:

$$S_i = \log(K) \log(\tau IG_i + 1)/\log(\tau + 1) \quad (3)$$

where $S_i$ is the output value.

Parameter τ controls the degree of enhancement of the small values. It is application dependent. For an echocardiography dataset we have set τ at 200 under guidance from domain experts.

Figure 7:
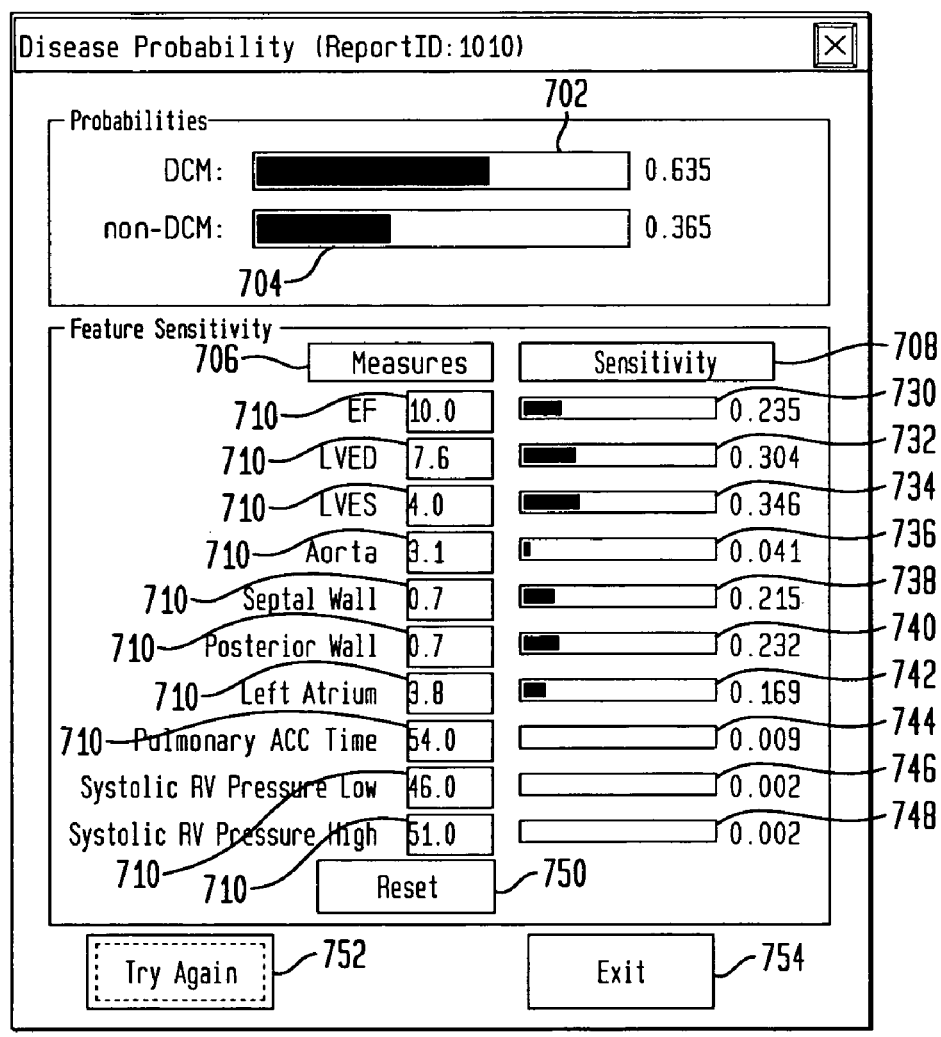
FIG. 7 is an exemplary user interface for the system of the present invention that illustrates feature sensitivity scoring in accordance with the present invention.

FIG. 7 illustrates an exemplary user interface in accordance with the present invention for manipulating feature sensitivity values. The interface provides an indication of parameter measurements 706 and the corresponding feature sensitivity values 708. FIG. 7 includes measurements 706-728 which are representative of various parameters determined by the physician as being important in making a particular medical diagnosis. In the present example, the condition being considered is DCM and the possible measurements (e.g., ejection fraction, septal wall circumference and pulmonary arc time) are indicated. It is to be understood by those skilled in the art that while measurements are indicated for each parameter listed in FIG. 7, feature sensitivity values can still be calculated if feature measurements are missing. For each parameter, a sensitivity value 730-748 is also indicated.

By activating the "try again" input 752, the probability of a particular condition, in this case DCM, is calculated based on the inputted measurements. In the present example, the probability of DCM 702 is indicated as 0.635 and the probability of non-DCM 704 is indicated as 0.365. The feature sensitivity values 708 provide guidance to the user as to which additional measurements would help determine the diagnosis. In the present example, the LVED 730 and LVES 732 measurements have the highest sensitivity values.

Figure 8:
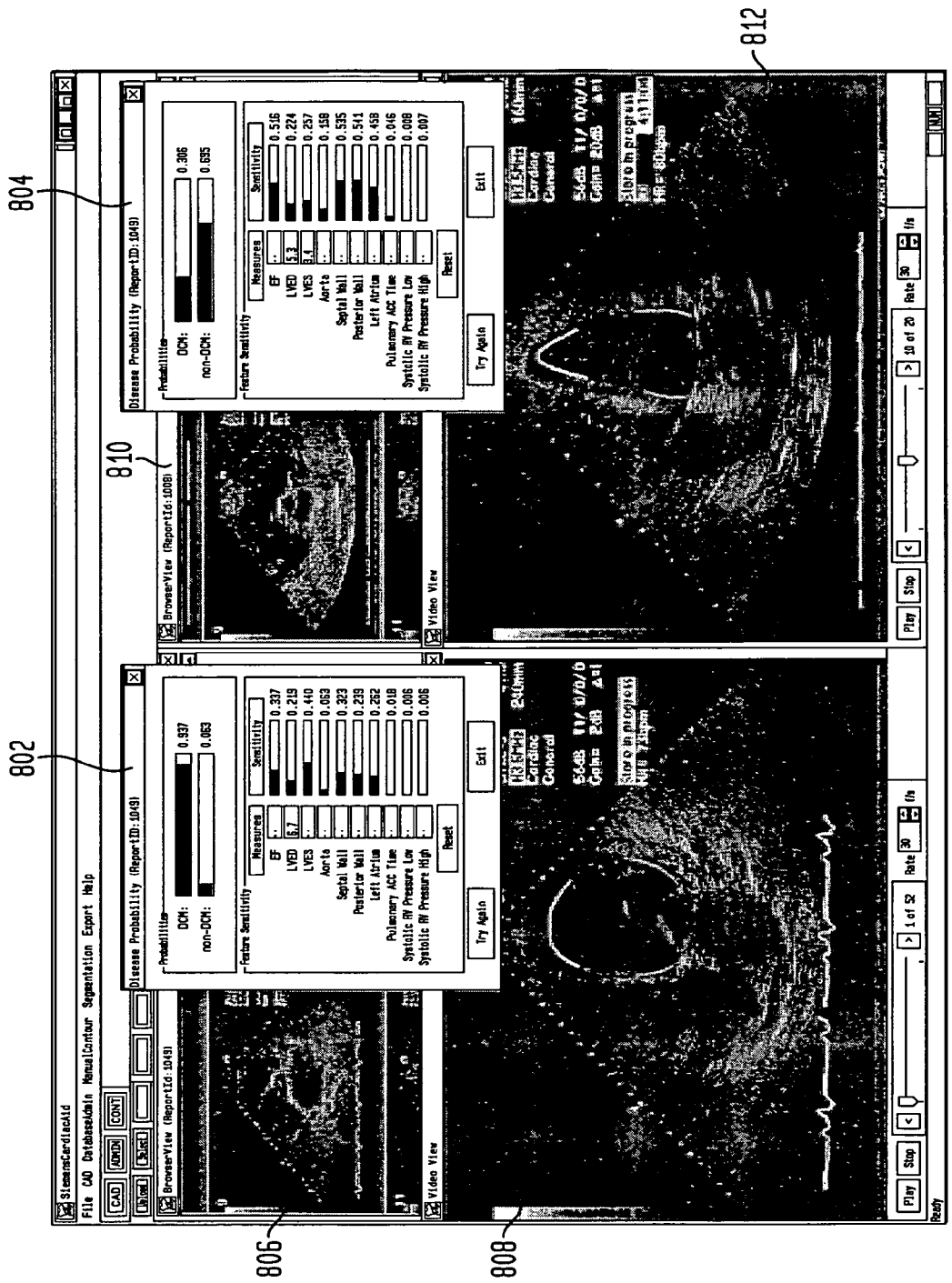
FIG. 8 is an exemplary user interface for the overall system in accordance with the present invention.

FIG. 8 illustrates an exemplary user interface in accordance with the present invention that can be used to incorporate all of the techniques disclosed herein. FIG. 8 illustrates a side by side comparison of the images 806, 808 for the case in question and a set of images 810, 812 from the training model database. The training images 810, 812 were selected based on a set of criteria determined by the physician or sonographer. The disease probabilities for the case in question are listed in interface 802 and the disease probabilities for the training model are listed in interface 804. In addition, interface 802 indicates the measurements taken in the case in question and the feature sensitivity values for all possible measurements. Likewise, interface 804 indicates the measurements taken for the training model and the feature sensitivity values for all possible measurements.

The physician can now consider all of the data in reaching a medical diagnosis. Alternatively, the physician can determine what additional measurements and/or tests should be performed in order to obtain a proper medical diagnosis. The physician can compare the image sets to determine if the training model retrieved displays a similar condition or can perform additional searches if the physician believes that better training models exist.

Having described embodiments for a system and method for a CAD system that provides decision support, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

We claim:

1. A method for assigning probability classification values to a set of identified classes based on a set of measurements taken during a medical procedure of a patient in order to provide decision support for rendering a medical diagnosis, the method comprising:
    sensing one or more medical measurements using a sensor and receiving data from the sensor representing the one or more medical measurements;
    analyzing the received data by applying decision rules and training models derived from knowledgebase data and prior physician input and using induction algorithms to learn probabilistic models;
    calculating probability values for the identified classes based on the analysis;
    determining sensitivity values for the one or more medical measurements based on the analysis; and
    rendering a medical diagnosis for the patient using the probability values for each identified class and the sensitivity measurements for the one or more measurements.

2. The method of claim 1 wherein the identified classes include classifications for one or more diseases.

3. The method of claim 2 wherein the one or more disease is Dilated Cardiomyopathy (DCM).

4. The method of claim 1 wherein the identified classes include a non-diseased classification.

5. The method of claim 4 wherein the non-diseased classification is non-Dilated Cardiomyopathy (non-DCM).

6. The method of claim 1 wherein the medical sensor is an ultrasound transducer.

7. The method of claim 1 wherein the medical procedure is an echocardiogram examination.

8. The method of claim 1 wherein the identified classes are linearly separable classes.

9. The method of claim 8 wherein the induction algorithms use non-parametric discriminant analysis.

10. The method of claim 9 wherein generative modeling is used in reduced discriminative space to obtain likelihood maps for each class.

11. The method of claim 9 wherein generative modeling is used in reduced discriminative space to obtain likelihood maps for each class.

12. The method of claim 1 wherein the identified classes have nonlinear class boundaries.

13. The method of claim 12 wherein the induction algorithms use kernel discriminant analysis.

14. The method of claim 13 wherein a Support Vector Model (SVM) is used to perform the kernel discriminant analysis.

15. The method of claim 1 wherein the probability values are provided in real time.

16. A method for assigning probability classification values to a set of identified classes based on a set of measurements taken during a medical procedure of a patient in order to provide decision support for rendering a medical diagnosis, the method comprising:
    sensing one or more medical measurements using a sensor and receiving data from the sensor representing the one or more medical measurements;
    analyzing the received data by applying decision rules and training models derived from knowledgebase data and prior physician input;
    calculating probability values for the identified classes based on the analysis;
    determining sensitivity values for the one or more medical measurements based on the analysis; and
    rendering a medical diagnosis for the patient using the probability values for each identified class and the sensitivity measurements for the one or more measurements,
    wherein the identified classes include classifications for one or more diseases, and the one or more diseases include Dilated Cardiomyopathy (DCM).

17. A method for assigning probability classification values to a set of identified classes based on a set of measurements taken during a medical procedure of a patient in order to provide decision support for rendering a medical diagnosis, the method comprising:
    sensing one or more medical measurements using a sensor and receiving data from the sensor representing the one or more medical measurements;
    analyzing the received data by applying decision rules and training models derived from knowledgebase data and prior physician input;
    calculating probability values for the identified classes based on the analysis;
    determining sensitivity values for the one or more medical measurements based on the analysis; and
    rendering a medical diagnosis for the patient using the probability values for each identified class and the sensitivity measurements for the one or more measurements,
    wherein the identified classes include a non-diseased classification, and wherein the non-diseased classification includes non-Dilated Cardiomyopathy (non-DCM).

18. A method for assigning probability classification values to a set of identified classes based on a set of measurements taken during a medical procedure of a patient in order to provide decision support for rendering a medical diagnosis, the method comprising:

sensing one or more medical measurements using a medical sensor and receiving data from the medical sensor representing the one or more medical measurements, wherein the medical sensor is an ultrasound transducer;

analyzing the received data by applying decision rules and training models derived from knowledgebase data and prior physician input;

calculating probability values for the identified classes based on the analysis;

determining sensitivity values for the one or more medical measurements based on the analysis; and rendering a medical diagnosis for the patient using the probability values for each identified class and the sensitivity measurements for the one or more measurements.

19. A method for assigning probability classification values to a set of identified classes based on a set of measurements taken during a medical procedure of a patient in order to provide decision support for rendering a medical diagnosis, the method comprising:

sensing one or more medical measurements using a sensor and receiving data from the sensor representing the one or more medical measurements;

analyzing the received data by applying decision rules and training models derived from knowledgebase data and prior physician input;

calculating probability values for the identified classes based on the analysis;

determining sensitivity values for the one or more medical measurements based on the analysis; and rendering a medical diagnosis for the patient using the probability values for each identified class and the sensitivity measurements for the one or more measurements, wherein the medical procedure is an echocardiogram examination.

* * * * *